United States Patent
Heil et al.

(10) Patent No.: US 7,148,207 B2
(45) Date of Patent: Dec. 12, 2006

(54) ORAL FLUDARA OF HIGH-PURITY FORMULATION WITH QUICK RELEASE OF ACTIVE INGREDIENT

(75) Inventors: Wolfgang Heil, Stelle (DE); Ulf Tistam, Wezembeek Oppem (BE); Ralph Lipp, Berlin (DE); Johannes-Wilhelm Tack, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/324,141

(22) Filed: Dec. 20, 2002

(65) Prior Publication Data

US 2003/0176391 A1   Sep. 18, 2003

Related U.S. Application Data

(60) Provisional application No. 60/404,399, filed on Aug. 20, 2002.

(30) Foreign Application Priority Data

Dec. 20, 2001   (DE)   ................................ 101 64 510

(51) Int. Cl.
*A61K 31/7076*   (2006.01)
*C07H 19/00*   (2006.01)

(52) U.S. Cl. .................. 514/48; 514/45; 536/28.2; 536/28.5; 536/28.52; 536/28.54; 536/28.55; 536/55.3; 536/27.12; 536/26.71; 424/457; 424/458; 424/460; 424/463; 424/469; 424/470

(58) Field of Classification Search .................. 514/45, 514/48; 424/457, 458, 460, 463, 464, 469, 424/470; 536/55.3, 27.12, 26.71, 28.2, 28.5, 536/28.52, 28.54, 28.55
See application file for complete search history.

(56) References Cited

U.S. PATENT DOCUMENTS

| | | | |
|---|---|---|---|
| 3,903,297 A | 9/1975 | Robert | |
| 4,188,378 A | 2/1980 | Montgomery | |
| 4,210,745 A | 7/1980 | Montgomery | |
| 4,357,324 A | 11/1982 | Montgomery et al. | |
| 5,296,589 A | 3/1994 | Blumberg | |
| 5,506,352 A | 4/1996 | Butler et al. | |
| 6,046,322 A * | 4/2000 | Tilstam et al. | 536/55.3 |
| 6,174,873 B1 * | 1/2001 | Wrenn, Jr. | 514/45 |
| 6,399,591 B1 | 6/2002 | Lee et al. | |

FOREIGN PATENT DOCUMENTS

| | | |
|---|---|---|
| DE | 19543052 A1 | 5/1997 |
| GB | 2124901 A | 2/1984 |
| WO | WO 97/39744 A1 | 10/1997 |
| WO | WO 99/63970 A1 | 12/1999 |
| WO | WO 01/14348 A2 | 6/2001 |
| WO | WO 01/41770 A2 | 6/2001 |
| WO | WO 01/43749 A2 | 6/2001 |

OTHER PUBLICATIONS

James M. Foran, David Oscier, Jennifer Orchard, Pharmacokinetic study of single doses of oral fludarabine phosphate in patients with "low-grade" non-hodgking's lymphoma, Journal of Clinical Oncology, May 1999, pp. 1574-1579.

* cited by examiner

*Primary Examiner*—Shaojia Anna Jiang
*Assistant Examiner*—Devesh Khare
(74) *Attorney, Agent, or Firm*—Millen, White, Zelano, Branigan, P.C.

(57) ABSTRACT

This invention relates to a quick-release tablet formulation with >99.19% pure fludara (high-purity fludara) as an active ingredient in a defined composition of residual contaminants.

12 Claims, No Drawings

ORAL FLUDARA OF HIGH-PURITY FORMULATION WITH QUICK RELEASE OF ACTIVE INGREDIENT

This application claims the benefit of the filing date of U.S. Provisional Application Ser. No. 60/404,399 filed Aug. 20, 2002.

This invention relates to a quick-release tablet formulation with >99.19% pure fludara (high-purity fludara)

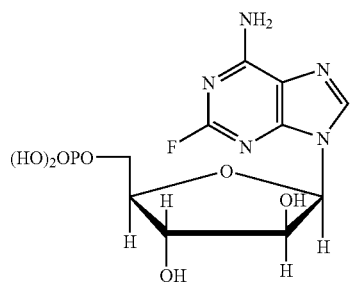

as active ingredient with a defined composition of residual contaminants.

Tablet formulations with fludara at a purity of <98% are already known. In the following works, i.a., various formulations and dosages are indicated (7 Modern Pharmaceutics, Chapters 9 and 10, Banker & Rhodes, Editors, 1979; Liebennan et al., Pharmaceutical Dosage Forms: Tablets, 1981; Ansel, Introduction to Pharmaceutical Dosage Forms 2nd Edition, 1976).

In U.S. Pat. No. 3,903,297, a tablet formulation that consists of active ingredient with lactose, microcrystalline cellulose, colloidal silicon dioxide and magnesium stearate is described by way of example (Example 2). The fact that a formulation can also contain crosscaramellose-Na is also described by way of example (Example 5). In WO 00/71134, in general tablet formulations that consist of lactose, microcrystalline cellulose, colloidal silicon dioxide, crosscaramellose-Na and magnesium stearate are described. Such a composition can also contain a chemotherapeutic substance.

From WO 97/40846, tablet coatings are known that contain hydroxypropyl methyl cellulose, titanium dioxide and pigments, such as, e.g., iron oxide pigments.

From WO 00/50423, tablet formulations are known that consist of lactose, microcrystalline cellulose, crosscaramellose-Na, etc., and that dissolve quickly.

U.S. Pat. No. 6,197,785, EP 1065206, EP 819430, EP 1065204 and EP 985666 describe tablet formulations that can be used for oral administration and that consist of lactose, microcrystalline cellulose, colloidal silicon dioxide, magnesium stearate, crosscaramellose-Na, talc, etc. As an active ingredient, i.a., fludara can be included.

Fludara formulations that have the active ingredient at a purity of >99.5% and disclose a defined composition of the contaminants of the active ingredient in the formulation are not known to date.

From WO 99/29710, the active ingredient fludara with a purity of >99.19% is known. Also in this prior art, however, no defined composition of the pure fludara that is contained in a formulation is provided.

It would therefore be desirable to have a stable tablet formulation that has fludara at high purity with a defined concentration of residual contaminants, that dissolves quickly and thus releases the active ingredient quickly.

It has now been found that a tablet formulation in which the active ingredient fludara is present at a purity of >99.19% in non-micronized but sieved form, with a defined concentration of residual contaminants, overcomes the drawbacks of the known tablets.

The tablet formulation comprises the active ingredient in an amount of 5 to 100 mg, preferably of 8 to 75 mg, especially preferably in an amount of 10 to 50 mg, selected in an amount of 10 to 20 mg.

The preferred formulation substances are lactose, colloidal silicon dioxide, microcrystalline cellulose (avicel), crosscaramellose-sodium (sodium carboxymethyl cellulose) and magnesium stearate.

Other formulation substances that are known in general to one skilled in the art are also conceivable, however.

The formulation substances in the tablet comprise a total amount of 100 to 250 mg, preferably a total amount of 120 to 200 mg, especially preferably a total amount of 130 to 180 mg.

A subject of this invention is thus a quick-release tablet formulation that comprises 1 to 100 mg of the active ingredient fludara at a purity of >99.19%, together with
  Lactose monohydrate,
  Colloidal silicon dioxide,
  Microcrystalline cellulose (avicel),
  Crosscaramellose-Na (sodium carboxymethyl cellulose),
  and magnesium stearate, characterized in that the contaminants in the fludara do not exceed a percentage as follows:
  0.02% 2-Fluoro-9-($\beta$-D-arabinofuranosyl)-9H-purine-6-amine,
  0.12% 6-Amino-9(5 -O-phosphono-$\beta$-D-arabinofuranosyl)-9H-purin-2-ol,
  0.02% 2-Fluoro-9H-purine-6-amine,
  0.02% 6-Amino-9H-purin-2-ol,
  0.05% 2-Fluoro-9-(5-O-phosphono-$\beta$-D-ribofuranosyl)-9H-purine-6-amine,
  0.1% 9-(3,5-O-diphosphono-$\beta$-D-arabinofuranosyl)-2-fluoro-9H-purine-6-amine,
  0.1% 9-(2,5-O-diphosphono-$\beta$-D-arabinofuranosyl)-2-fluoro-9H-purine-6-amine,
  0.02% 2-Fluoro-9-(5-O-phosphono-$\beta$-D- arabinofuranosyl)-9H-purine-6-amine,
  0.06% 2-Ethoxy-9-(5-O-phosphono-$\beta$-D- arabinofuranosyl)-9H-purine-6-amine,
  0.02% 2-(6-Amino-9H-purin-2-yl)-9-(5-O-phosphono-$\beta$-D-arabinofuranosyl)-9H-purine-6-amine and O,O'-bis [2-(6-amino-2-fluoro-9H-purin-9-yl)-5-deoxy-$\alpha$-D-arabinofuranos-5-yl]-phosphate,
  0.1% 9-(2-Chloro-2-deoxy-5-phosphono-$\beta$-D-arabinofuranosyl)-2-fluoro-9H-purine-6-amine and
  0.1% 9-(2,5-Anhydro-$\beta$-D-arabinofuranosyl)-2-fluoro-9H-purine-6-amine.

Preferred is a quick-release tablet formulation that comprises
  1 to 70.00 mg of the active ingredient fludara at a purity of >99.19%, together with 50 to 100 mg of lactose monohydrate, 0.1 to 5 mg of colloidal silicon dioxide,
40 to 100 mg of microcrystalline cellulose (avicel),
1 to 10 mg of crosscaramellose-Na (sodium carboxymethyl cellulose) and
0.5 to 10 mg of magnesium stearate.

Especially preferred are those quick-release tablet formulations that comprise
1 to 50.00 mg of the active ingredient fludara at a purity of >99.19%, together with 60 to 90 mg of lactose monohydrate,
0.5 to 1 mg of colloidal silicon dioxide,
50 to 90 mg of microcrystalline cellulose (avicel),
1.5 to 5 mg of crosscaramellose-Na (sodium carboxymethyl cellulose) and
1 to 3 mg of magnesium stearate.

Selected is such a quick-release table formulation that comprises 10 mg of the active ingredient fludara at a purity of >99.19%, together with
74.75 mg of lactose monohydrate,
0.75 mg of colloidal silicon dioxide,
60.00 mg of microcrystalline cellulose (avicel),
3.00 mg of crosscaramellose-Na (sodium carboxymethyl cellulose) and
1.5–2.00 mg of magnesium stearate.

Preferred are also those formulations that comprise the active ingredient fludara at a purity of >99.37%.

Still more preferred are those formulations that comprise the active ingredient fludara at a purity of >99.57%.

Especially preferred are those formulations that comprise the active ingredient fludara at a purity of >99.80%.

Especially preferred are those formulations that comprise the active ingredient fludara at a purity of >99.85%.

The formulations according to the invention are processed into molding compounds according to generally known methods, and said molding compounds are then pressed into tablet cores. These tablet cores can be provided with coatings with generally known methods. In principle, all coatings that are known to one skilled in the art can be used. A preferred coating comprises, e.g., the following components:

1 to 5 mg, preferably 1 to 3 mg, especially preferably 2.250 mg of hydroxypropyl methyl cellulose,
0.1 to 1 mg, preferably 0.1 to 0.8 mg, especially preferably 0.450 mg of talc,
0.1 to 5 mg, preferably 0.1 to 2 mg, especially preferably 1.187 mg of titanium dioxide,
0.01 to 0.1 mg, preferably 0.01 to 0.05 mg, especially preferably 0.036 mg of yellow iron oxide pigment, and
0.01 to 0.1 mg, preferably 0.01 to 0.05 mg, especially preferably 0.036 mg of red iron oxide pigment.

These coatings are also subjects of this invention.

The tablet formulations according to the invention can be used for the production of a medication for treating cancer.

This invention thus also comprises the use of the formulations according to the invention for the production of a medication for treating cancer.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples describe the production of the fludara of high-purity tablet formulations according to the invention as well as a comparison of the conventional composition of <98% pure fludara with >99.19% pure fludara.

EXAMPLE 1

Production of a Tablet Formulation

For the production of a tablet formulation according to the invention, the active ingredient fludara (fludarabine phosphate) is first sieved and then processed with lactose monohydrate, microcrystalline cellulose (avicel) and colloidal silicon dioxide to an approximately 30% dry mixture. The mixture is then also sieved. The quality or particle size is examined by means of sieve analysis. Crosscaramellose sodium (sodium carboxymethyl cellulose) and magnesium stearate in additional mixed sequences are then added successively to the dry mixture.

The molding compound is pressed into tablet cores.

A thus produced tablet formulation comprises, for example, the following individual components:

| | |
|---|---|
| Fludara > 99.19% high-purity | 10.00 mg |
| Lactose monohydrate | 74.75 mg |
| Colloidal silicon dioxide | 0.75 mg |
| Microcrystalline cellulose (avicel) | 60.00 mg |
| Crosscaramellose-Na | 3.00 mg |
| (Sodium carboxymethyl cellulose) | |
| Magnesium stearate | 1.5–2.00 mg |

The tablet cores are then painted with an aqueous film suspension. Such a film coating comprises, for example, the following components:

| | |
|---|---|
| Hydroxypropyl methyl cellulose | 2.250 mg |
| Talc | 0.450 mg |
| Titanium dioxide | 1.187 mg |
| Iron oxide pigment, yellow | 0.036 mg |
| Iron oxide pigment, red | 0.036 mg |

The total weight of the tablet is 154 mg.

The thus produced film tablets can then be further processed. The film tablets can be packaged in, e.g., Alu-blisters, by which the stability of the formulation is ensured.

EXAMPLE 2

Comparison of a conventional composition of <98% (97.67%) pure fludara with >99.19%, or >99.57% pure fludara and 99.19% fludara that is purified with an ion exchanger.

The results are presented in the table below.

| Compound Nr. | Structural Formula | Chemical Name According to IUPAC | Proportion of Contaminants [%] | | | | |
|---|---|---|---|---|---|---|---|
| | | | <98% Pure Fludara | Ion Exchange Column | Batch 1* | Batch 2* | Batch 3* |
| 1 | | 2-Fluoro-9-(β-D-arabino-furanosyl)-9H-purine-6-amine | 0.14 | 0.01 | 0.02 | 0.01 | 0.01 |
| 2 | | 6-Amino-9(5-O-phosphono-β-D-arabino-furanosyl)-9H-purin-2-ol | 1.38 | 0.33 | 0.11 | 0.09 | 0.12 |
| 3 | | 2-Fluoro-9H-purine-6-amine | 0.03 | 0.05 | 0.02 | 0.02 | 0.02 |
| 4 | | 6-Amino-9H-purin-2-ol | 0.25 | 0.02 | <0.02 | 0.02 | <0.02 |
| 5 | | 2-Fluoro-9-(5-O-phosphono-β-D-ribofuran-osyl)-9H-purine-6-amine | 0.02 | 0.02 | 0.04 | 0.03 | 0.05 |

-continued

| Compound Nr. | Structural Formula | Chemical Name According to IUPAC | Proportion of Contaminants [%] | | | | |
|---|---|---|---|---|---|---|---|
| | | | <98% Pure Fludara | Ion Exchange Column | Batch 1* | Batch 2* | Batch 3* |
| 6 | | 9-(3,5-O-di-phosphono-β-D-arabino-furanosyl)-2-fluoro-9H-purine-6-amine | 0.06 | 0.06 | 0.1 | 0.09 | 0.08 |
| 7 | | 9-(2,5-O-di-phosphono-β-D-arabino-furanosyl)-2-fluoro-9H-purine-6-amine | 0.03 | 0.02 | 0.1 | 0.09 | 0.08 |
| 8 | | 2-Fluoro-9-(5-O-phosphono-β-D-arabino-furanosyl)-9H-purine-6-amine | 0.02 | 0.01 | <0.02 | <0.02 | <0.02 |
| 9 | | 2-Ethoxy-9-(5-O-phosphono-β-D-arabino-furanosyl)-9H-purine-6-amine | 0.26 | 0.02 | 0.06 | 0.01 | 0.01 |

-continued

| Compound Nr. | Structural Formula | Chemical Name According to IUPAC | <98% Pure Fludara | Ion Exchange Column | Batch 1* | Batch 2* | Batch 3* |
|---|---|---|---|---|---|---|---|
| 10 | | 2-(6-Amino-9H-purin-2-yl)-9-(5-O-phosphono-β-D-arabino-furanosyl)-9H-purine-6-amine | 0.05 | 0.14 | 0.02 | 0.02 | 0.02 |
| | and | | | | | | |
| 11 | | O,O'-Bis[2-(6-amino-2-fluoro-9H-purin-9-yl)-5-deoxy-α-D-arabino-furanos-5-yl]-phosphate, ammonium salt | | | | | |
| 12 | | 9-(2-Chloro-2-deoxy-5-phosphono-β-D-arabino-furanosyl)-2-fluoro-9H-purine-6-amine | 0.05 | 0.01 | 0.06 | 0.03 | 0.1 |
| 13 | | 9-(2,5-Anhydro-β-D-arabino-furanosyl)-2-fluoro-9H-purine-6-amine | 0.04 | 0.12 | 0.06 | 0.03 | 0.1 |
| % Contaminants- Total: | | | 2.33 | 0.81 | <0.63 | <0.43 | <0.63 |
| % Purity | | | 97.67 | 99.19 | >99.37 | >99.57 | >99.37 |

*High-purity Fludara

The results show that a formulation that consists of commercially available fludara (maximum 97.67% fludara) or a formulation with fludara that is purified via an ion exchanger (maximum 99.19% fludara) has considerably more contaminating by-products than the high-purity fludara that is contained in the formulations according to the invention (>99.37% to >99.57% fludara).

With conventional purification processes, such as the very potent ion exchange chromatography, only a quite moderate degree of purity can be achieved.

The fludara formulations according to the invention contain the high-purity fludara that is released via the sodium salt that is already described in WO 99/29710. A still higher degree of purity of the fludara can be produced with the potassium salt (99.8%) or with the lithium salt (99.85%).

The entire disclosures of all applications, patents and publications, cited herein and of corresponding German Application No. 101 64-510.4, filed Dec. 20, 2001, and U.S. Provisional Application Ser. No. 60/404,399, filed Aug. 20, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A quick-release tablet formulation that comprises
   1 to 100 mg of the active ingredient fludarabine phosphate having a purity of >99.19%,
   lactose monohydrate,
   colloidal silicon dioxide,
   microcrystalline cellulose,
   sodium carboxymethyl cellulose, and
   magnesium stearate,
   wherein said formulation releases fludarabine phosphate with a quick release profile, and
wherein the contaminants in the fludarabine-phosphate do not exceed:
   0.02% 2-fluoro-9-(β-D-arabinofuranosyl)-9H-purine-6-amine,
   0.12% 6-amino-9(5-O-phosphono-β-D-arabinofuranosyl)-9H-purin-2-ol,
   0.02% 2-fluoro-9H-purine-6-amine,
   0.02% 6-amino-9H-purin-2-ol,
   0.05% 2-fluoro-9-(5-O-phosphono-β-D-ribofuranosyl)-9H-purine-6-amine,
   0.1% 9-(3,5-O-diphosphono-β-D-arabinofuranosyl)-2-fluoro-9H-purine-6-amine,
   0.1% 9-(2,5-O-diphosphono-β-D-arabinofuranosyl)-2-fluoro-9H-purine-6-amine,
   0.02% 2-fluoro-9-(5-O-phosphono-β-D-arabinofuranosyl)-9H-purine-6-amine,
   0.06% 2-ethoxy-9-(5-O-phosphono-β-D-arabinofuranosyl)-9H-purine-6-amine,
   0.02% 2-(6-amino-9H-purin-2-yl)-9-(5-O-phosphono-β-D-arabinofuranosyl)- 9H-purine-6-amine and O,O'-bis[2-(6-amino-2-fluoro-9H-purin-9-yl)-5-deoxy-α-D-arabinofuranos-5-yl]-phosphate,
   0.1% 9-(2-chloro-2-deoxy-5-phosphono-β-D-arabinofuranosyl)-2-fluoro-9H-purine- 6-amine, and
   0.1% 9-(2,5-anhydro-β-D-arabinofuranosyl)-2-fluoro-9H-purine-6-amine.

2. A quick-release tablet formulation according to claim 1, which comprises 1–70 mg of the active ingredient fludarabine phosphate having a purity of >99.19%,
   50–100 mg of lactose monohydrate,
   0.1–5 mg of colloidal silicon dioxide,
   40–100 mg of microcrystalline cellulose,
   1–10 mg of sodium carboxymethyl cellulose and
   0.5–10 mg of magnesium stearate.

3. A quick-release tablet formulation according to claim 1, which comprises 1–50 mg of the active ingredient fludarabine phosphate having a purity of >99.19%,
   60–90 mg of lactose monohydrate,
   0.5–1 mg of colloidal silicon dioxide,
   50–90 mg of microcrystalline cellulose,
   2.5–5 mg of sodium carboxymethyl cellulose and
   1–3 mg of magnesium stearate.

4. A quick-release tablet formulation according to claim 1, which comprises 10 mg of the active ingredient fludarabine phosphate having a purity of >99.19%,
   74.75 mg of lactose monohydrate,
   0.75 mg of colloidal silicon dioxide,
   60.00 mg of microcrystalline cellulose,
   3.00 mg of sodium carboxymethyl cellulose and
   1.5–2.00 mg of magnesium stearate.

5. A quick-release tablet formulation according to claim 1, which comprises the active ingredient fludarabine phosphate having a purity of >99.37%.

6. A quick-release tablet formulation according to claim 1, which comprises the active ingredient fludarabine phosphate having a purity of >99.57%.

7. A quick-release tablet formulation according to claim 1, which comprises the active ingredient fludarabine phosphate having a purity of >99.80%.

8. A quick-release tablet formulation according to claim 1, which comprises the active ingredient fludarabine phosphate having a purity of >99.85%.

9. A quick-release tablet formulation according to claim 1, wherein the tablet has a core encased by a coating comprising:
   1–5 mg of hydroxypropyl methyl cellulose,
   0.1–1 mg of talc,
   0.1–5 mg of titanium dioxide,
   0.01–0.1 mg of yellow iron oxide pigment and
   0.01–0.1 mg of red iron oxide pigment.

10. A quick-release tablet formulation according to claim 1, wherein the tablet has a core encased by a coating, comprising:
    1–3 mg of hydroxypropyl methyl cellulose,
    0.1–0.8 mg of talc,
    0.1–2 mg of titanium dioxide,
    0.01–0.05 mg of yellow iron oxide pigment and
    0.01–0.05 mg of red iron oxide pigment.

11. A quick-release tablet formulation according to claim 1, wherein the tablet has a core encased by a coating, comprising:
    2.250 mg of hydroxypropyl methyl cellulose,
    0.450 mg of talc,
    1.187 mg of titanium dioxide,
    0.036 mg of yellow iron oxide pigment and
    0.036 mg of red iron oxide pigment.

12. A medication for treating cancer comprising a tablet formulation according to claim 1.

* * * * *